United States Patent [19]

Snow et al.

[11] Patent Number: 4,993,876
[45] Date of Patent: Feb. 19, 1991

[54] METHOD AND APPARATUS FOR PROTECTIVE ENCAPSULATION OF STRUCTURAL MEMBERS

[75] Inventors: Richard K. Snow, Gallatin; Milton W. Ellisor, Jr., Houston, both of Tex.

[73] Assignee: 501 Sandoz, Ltd., Switzerland

[21] Appl. No.: 373,691

[22] Filed: Jul. 3, 1989

Related U.S. Application Data

[60] Continuation of Ser. No. 247,846, Sep. 22, 1988, abandoned, which is a division of Ser. No. 874,500, Jun. 16, 1986, Pat. No. 4,876,896.

[51] Int. Cl.⁵ ............................................. E02D 5/60
[52] U.S. Cl. ...................................... 405/216; 52/725
[58] Field of Search ............... 405/211, 216, 260, 231, 405/232, 257; 52/724, 725, 727, 728; 249/1; 264/32, 35

[56] References Cited

U.S. PATENT DOCUMENTS

| | | | |
|---|---|---|---|
| 3,861,155 | 1/1975 | Steinberg et al. | 405/260 |
| 4,019,301 | 4/1977 | Fox | 405/216 X |
| 4,439,070 | 3/1984 | Dimmick | 405/216 |

FOREIGN PATENT DOCUMENTS 1494072 12/1977 United Kingdom ................ 405/216

Primary Examiner—David H. Corbin
Attorney, Agent, or Firm—Dodge, Bush & Moseley

[57] ABSTRACT

The method and apparatus for forming an encapsulation or encasement about a structural member that is particularly well suited for use in a marine environment is disclosed. A two component polymer system for protective and repair encapsulation is pumpable in two separate streams to the location of the structural member to be encapsulated. The two reactive components are combined in a static mixer immediately prior to being injected within the surrounding translucent jacket. By combining the reactive components immediately prior to use, premature set up is avoided and the resulting grout may be directed to flow upwardly in the jacket for enhancing final properties. By suitable coloring of the components, visual monitoring of the final mxing and distribution in the translucent form or jacket of the encapsulation material may be monitored. A field test for determining bond strength of the encapsulation polymer to the structural member is also disclosed.

25 Claims, 4 Drawing Sheets

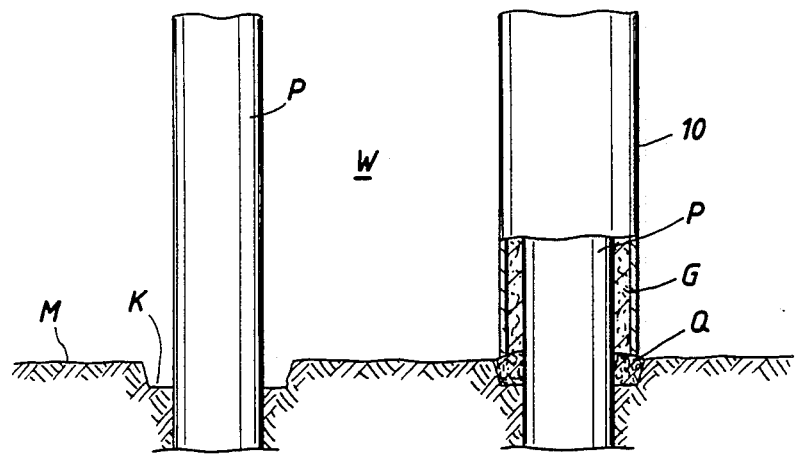
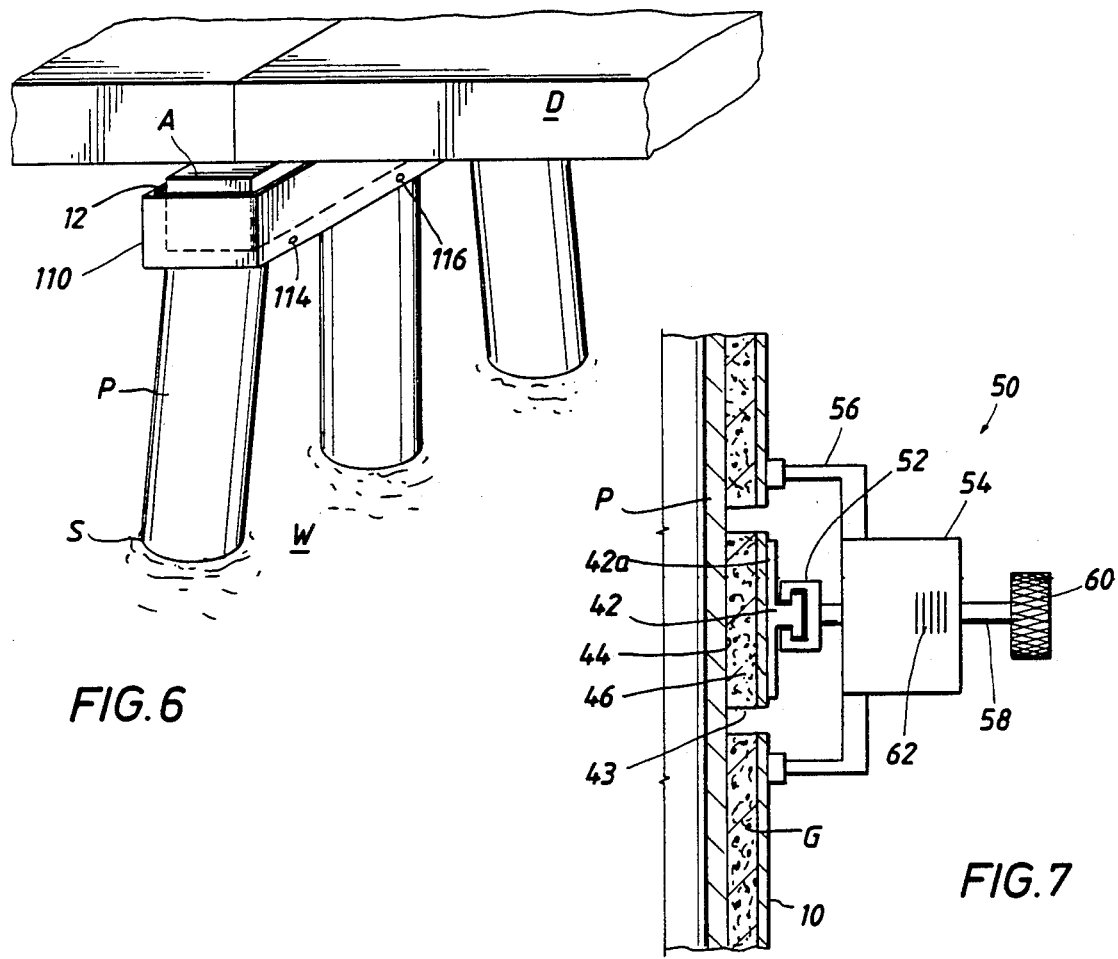

METHOD AND APPARATUS FOR PROTECTIVE ENCAPSULATION OF STRUCTURAL MEMBERS

This application is a continuation of application Ser. No. 247,846, filed Sept. 22, 1988, now abandoned which is a division of application Ser. No. 874,500 filed June 16, 1986, now U.S. Pat. No. 4,876,896.

BACKGROUND OF THE INVENTION

FIELD OF THE INVENTION

This invention relates generally to the field of encasement or encapsulation of structural members and more particularly to a polymer encapsulation for repair or protection of such structural members.

BACKGROUND ART

The use of piles or piers as structural supports for wharfs, bridges or other marine environment structures is well known. The usual materials of construction for such marine structures are concrete, steel, wood or a combination or composite of two or more of these materials. All three of these materials of construction are vulnerable to corrosion or deterioration above, at or below the water line. Such support piles may be damaged or subject to deterioration by salt water, corrosive pollution, cycles of wetting and drying, cycles of freezing and thawing and electrolysis. Erosion, marine organisms, mechanical impact, water content and abrasion may also cause premature failures of even properly designed structures.

Protecting piles, risers, piers, supports, columns or other load supporting structural members used in a marine environment is often times unreliable and time consuming. Some alternatives or methods for arresting deterioration in marine support structures such as vinyl wraps, protective coatings, and concrete encasements have been tried, but with inconsistent results. These means of repair or protection are only short term solutions and may be unfeasible for certain structures. For instance, vinyl wraps are subject to puncture and tearing from mechanical impact. Most protective coatings eventually fail due to inadequate surface preparation, improper application, ultra violet light exposure, mechanical wear or pinhole defects. Concrete encasements used as repair and protective encapsulation are often unsuitable as they result in too heavy an additional load for the structure to support and the porous encapsulation may be subject to penetration by chlorides and marine organisms.

A known repair and protective procedure for damaged, as well as new piers or piles, provides for encapsulation in a corrosion resistant polymer jacket. By pouring a flowable mixed epoxy material into a surrounding form or jacket, the epoxy grout would solidify or harden about the pile, thus sealing off oxygen and preventing corrosion as well as structurally repairing the pile. For an example of such protective and repair encapsulation see U.S. Pat. No. 4,019,301 to Fox and the references cited therein which are hereby all fully incorporated herein by this reference. While an improvement over prior practice, the Fox method can often be unreliable. By simply pouring the batch mixed epoxy encapsulating material into the surrounding form, no assurance is obtained that gravity flow will effect elimination of voids or seams by completely filling the surrounding form or that premature set up of the encapsulating material will not channel the filling material flow. Through the process of pouring the epoxy into the submerged fiberglass jacket or form, water can dilute, entrain or mix with the epoxy, thus adversely affecting the engineering properties of the protective or repair system. The pouring procedure also can create holidays or non-bonded cold joints between pours, be very time consuming, messy and impractical for structures that are not readily accessible. Furthermore, no provision was made for verifying, by visual observation or otherwise, that the encapsulating material fully filled the jacket form or for field verifying that adequate structural bonding to the structure has occurred.

Pumps have been developed to place mixed or catalyzed epoxy encapsulating material in the surrounding jacket. This method offered a substantial improvement over batch pouring, but still presented a problem due to the gravity driven flow of the catalyzed epoxy grout used to fill the jacket or form and the catalyzed epoxy grout setting up prematurely in hoses and equipment. Also, the end product properties are highly dependant upon proper mixing of each batch by personnel in the field. If inexperienced personnel are used, inconsistent batches of epoxy are often the result.

The repair and protective encapsulation process was normally accomplished by installing custom built prefabricated jacket about the piling to form the continuous annular void. After a lower seal for the grout filling was effected between pile and jacket, the two-component polymer was then mixed and poured or pumped into the top of the void for filling and curing in place. As a polymer grout has a limited "pot life" or working time after mixing with the catalyst, any unanticipated delay would result in loss of the mixed polymer from undesired hardening or a serious deterioration in quality. Premature setting or solidifying of the polymer grout, usually an epoxy based resin, could also result in lost time for cleaning as well as requiring hose and equipment replacement. Because of this limited "pot life", encapsulation was essentially an individual or "batch operation". While this is acceptable if only a few piles are to be repaired or protected, it is much too costly and unreliable for entire structures, such as a wharf or a causeway, which may have hundreds of piles.

The batch processing and pouring had a severe additional limitation as the bond strength between the encapsulating material and the load supporting or structural member, to form a unitary structure, was usually inconsistent. This drawback was magnified by the unavailability of a suitable, simple field test or instrument to measure or verify this vital property or characteristic.

SUMMARY OF THE INVENTION

The present invention relates to the field of encapsulating or encasing of all or part of a structural member for either protection, repair or both. The portion of the structural member to be encapsulated is cleaned and then surrounded by a translucent jacket, that forms a continuous annular void between the jacket and the portion of the structural member to be repaired and/or protected. The lower end of the jacket is sealed to the structural member to contain the epoxy grout or encapsulating material. The jackets are provided with a plurality of longitudinally spaced ports to enable continuous injection of the flowable epoxy grout material into the void area, where it flows upwardly in the void, displacing any water that may be in the jacket, prior to hardening in place, to assure a homogeneous, dense, holiday-free encapsulation.

The encapsulating material or grout, preferably epoxy based, is supplied in two separate flowable premixed components by pumping each component under pressure through separate hoses to a discharge control manifold where the grout is finally mixed immediately prior to being injected into the encapsulation jacket. This results in a consistent mix of encapsulation grout being injected into the jacket and prevents premature activation by the catalyst with undesired resulting setup or hardening of the epoxy and damage to the pumping equipment. Pumping capacity of the injection system is designed to prevent formation of seams or cold joints such as are formed between poured "batches" which can destroy the effectiveness of the encapsulation material. Suitable coloring is added to the separate grout components to indicate and assure proper and complete mixing and as well as proper filling of the translucent jacket with a homogeneous grout.

A method and apparatus for field testing of the bond strength between the structural member and the encapsulation grout is provided to insure proper adhesion and strength.

BRIEF DESCRIPTION OF THE DRAWINGS

FIG. 5 is, a view similar to a portion of FIG. 3;

FIG. 6 is a perspective view of partial encapsulation of a horizontal structural member; and FIG. 7 is a side view, partially in section, of a bond strength field test unit in the operating position.

DESCRIPTION OF THE PREFERRED EMBODIMENT

The method and apparatus of the present invention of encasement or encapsulation of a structural member is illustrated in the Figures as applied to a marine environment structure such as a causeway or wharf D. It is to be understood that the use of the present invention for repair or protection is not limited to any specific application, location or environment, but is particularly well suited for use in a marine environment where horizontal, oblique or vertical structural supports members or portions thereof may be constantly submerged or may be submerged only from time to time.

Figure 1:
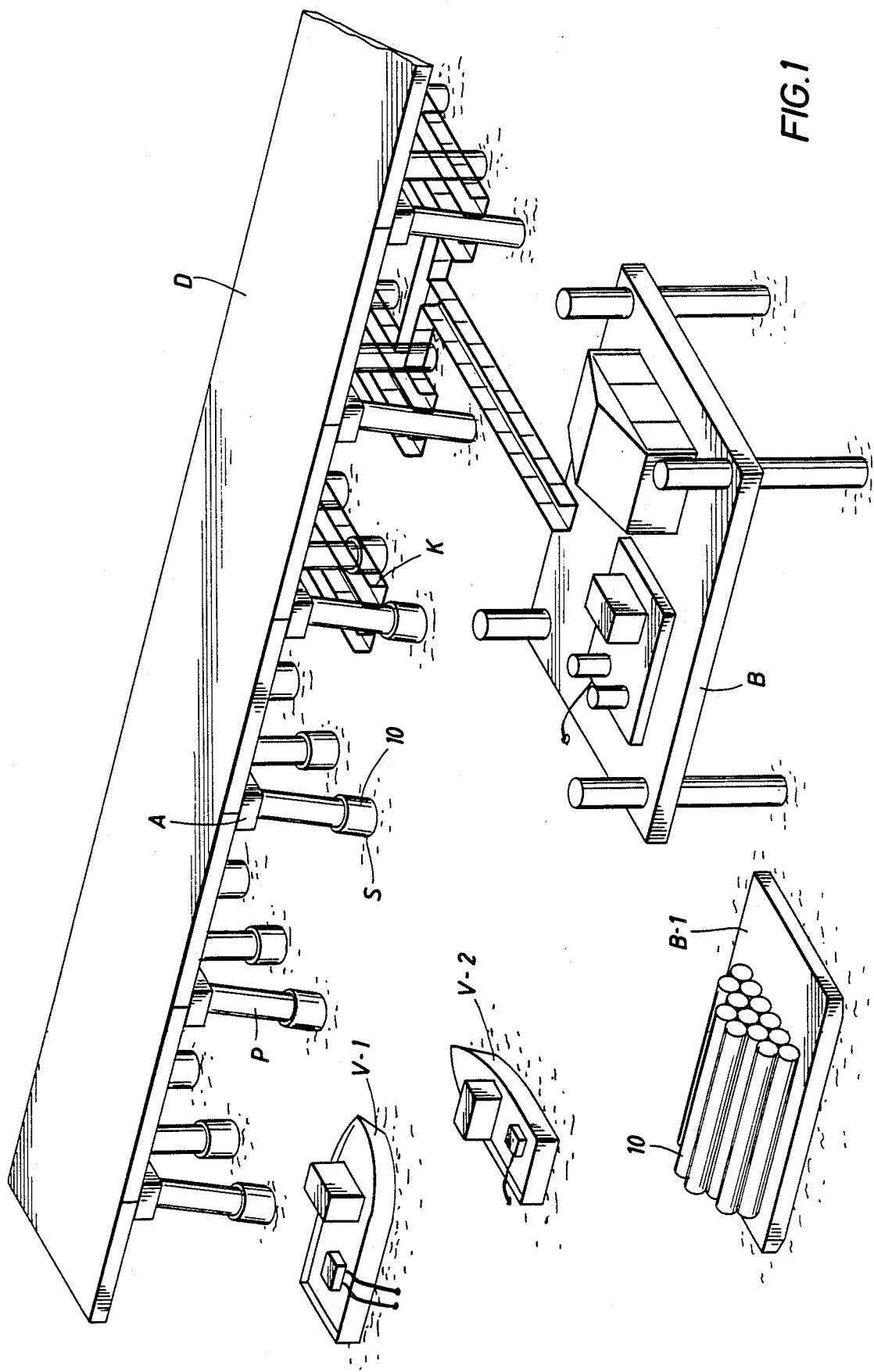
FIG. 1 is a perspective view of a wharf or causeway having the support piers or piles encapsulated in accordance with the present invention.
Figure 2:
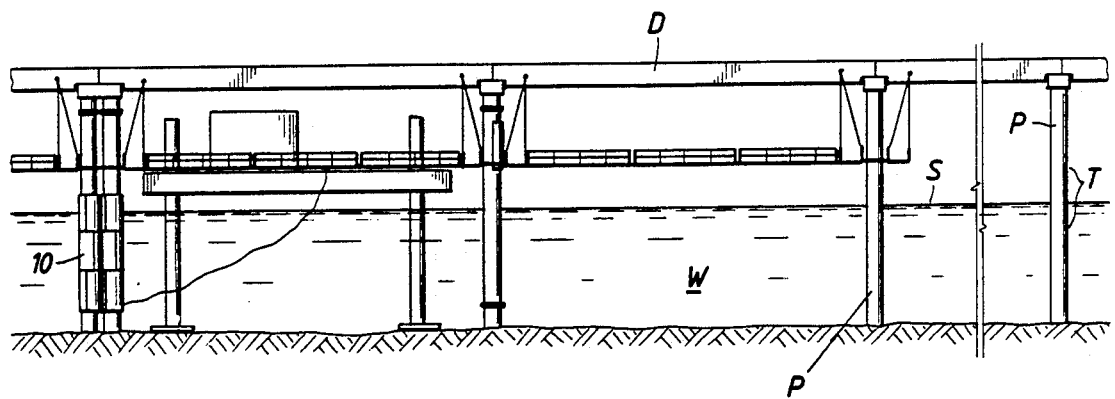
FIG. 2 is a side view, in section, of the wharf or causeway having the piles encapsulated in accordance with the present invention.

In the illustrated embodiment, the horizontal support surface wharf D is supported by a plurality of vertical or substantially vertically oriented structural members or piles P arranged in a preselected manner to maintain the horizontal structural support members or beams A forming the wharf D in the desired position. As best illustrated in FIG. 2, a portion of each pile P may be completely submerged in and constantly exposed to the deleterious affects of water W while a certain zone of the pile P near the water surface S, called either the tidal zone or splash zone T, is sometimes dry and sometimes wet due to wave action and tidal variations in water level. Above the tidal zone T, the piles P may not be exposed to the water on any normal basis. Furthermore, it may be desired to encapsulate or encase only the portion of the pile P adjacent the tidal zone T and not the portion of the pile P constantly submerged. The present invention provides a method and apparatus for encapsulating or encasing all or any desired portion of a structural or load carrying beam or pile P and should not be considered limited to any particular orientation, horizontal, oblique or vertical of any structural member or portion thereof. Nor should the present invention be considered limited to a structural member of any particular shape, configuration or cross-section. For purposes of this disclosure, the present invention will be described with emphasis on repair and protection of a partially submerged vertical pile, but it will be understood that the present invention is not so limited as noted above. Also the terms encapsulation and encasement and their variations will be used interchangeably herein and will have identical meanings or definitions for purposes of this disclosure.

In the marine environment a portion of the work done during the pile P encapsulation may be performed by a crew of divers F using diving equipment and techniques. Such diving techniques and equipment are conventional, well known to those skilled in the art, and form no part of the present invention. Where access to the structural member to be encapsulated may be achieved without the use of divers F, the divers may not be used at a significant cost saving.

In the illustrated embodiment, all support for the divers F is provided from vessels V-1 and V-2 and not from the wharf D itself. It being understood that if the wharf D is available, the support equipment and personnel for the divers F may be located thereon. However, it should be understood that the present invention can be utilized or performed without interrupting the use of the wharf D, causeway, bridge or other structure for its intended purpose. A work barge B, preferably of the Jack-up Type, may be provided to serve as a tender work area and to support and store the necessary supplies and equipment for performing the present invention. A conventional barge B-1 may be used to supplement the tender B if desired. Also in this regard, platforms K for other workmen may be suspended from the wharf D to enable convenient placement of the forms or jackets that will be described in greater detail hereinafter. It being understood that the work platforms K could be dispensed with and either small boats (not illustrated) or the divers F used to place or assist in placing the pile jackets 10 without departing from the scope of the present invention. It is preferable that such access work platforms K be utilized as it greatly expedites the performing of the method of the present invention.

Cleaning

Prior to encapsulation, it will be necessary to prepare and clean the portion of the pile P to be encapsulated. For submerged portions of each pile P, the pile cleaning is a two step process or operation illustrated in FIG. 3 in which the first phase is done no more than seven days prior to the encapsulation. The first cleaning may be done by divers F using pneumatic powered rotary brushes and scrapers tools C and is intended to remove any deposits or built up material accumulated on the pile. If the pile P is newly installed, this power tool C cleaning step may not be required.

The final submerged portion pile cleaning is done no more than twenty four hours prior to encapsulation to insure a good bond between the encapsulating material and the pile P. This cleaning is preferably done by divers F using high pressure sand or water blasters or jets J, but any suitable pile surface preparation and cleaning method may be employed. Diver manipulated video camera V may be used to remotely visually inspect and record each step of the encapsulation process.

In bio-active water environments, the cleaning step may also include the further step of circulating a biological inhibitor solution into the jacket 10. Such solution is normally injected after the final cleaning, and jacket installation and allowed to remain in the jacket 10 until displaced by the epoxy grout used to encapsulate the pile P.

Surface preparation and cleaning of the portion of the pile P above the water line W may be accomplished in a single step of high pressure water or sand blasting with jet J. This is preferably done immediately before encapsulation.

Jacket Construction

The encapsulation material containment form or jacket 10 is preferably formed of chemically inert and corrosion resistant fiberglass reinforced polyester, one-eighth (⅛) inch thick, that is made of one or more longitudinally extending seams to enable placement about the pile P. For ease of installation, the jacket 10 is of flexible construction. The jacket 10 is dimensioned so when properly positioned about the circular pile P to be encapsulated, a continuous surrounding annular void 12 (FIG. 4) is formed between the pile P and the jacket 10 for receiving and holding the encapsulating grout during and after curing or hardening. To insure and maintain concentric centering or proper placement of the jacket 10 about the circular cross-section pile P, suitable inwardly projecting stand-off or centering lugs 10a may be formed or placed at a plurality of suitable locations on the inner surface of the jacket. Such lugs 10a, which may or may not be externally L threadedly adjustable as illustrated at 10b, should be formed to enable free flow of the epoxy material in the void 12. For convenience of installation, the jacket 10 may be formed in easily handled sections which are assembled in an end-to-end relationship to form the desired area of encapsulation of the pile P.

By suitable jacket design, piles of other cross-section configuration may also be encapsulated. If only partial encapsulation is desired, the jacket 10 may be designed to only partially surround the structural member for encapsulating only a portion of the member. In such cases, the void 12 will be continuous over the portion of the member to be encapsulated. Such variations in encapsulation and jacket 10 design will be dictated by the pile P repair and protection desired and will be apparent to those skilled in the art.

Figure 3:
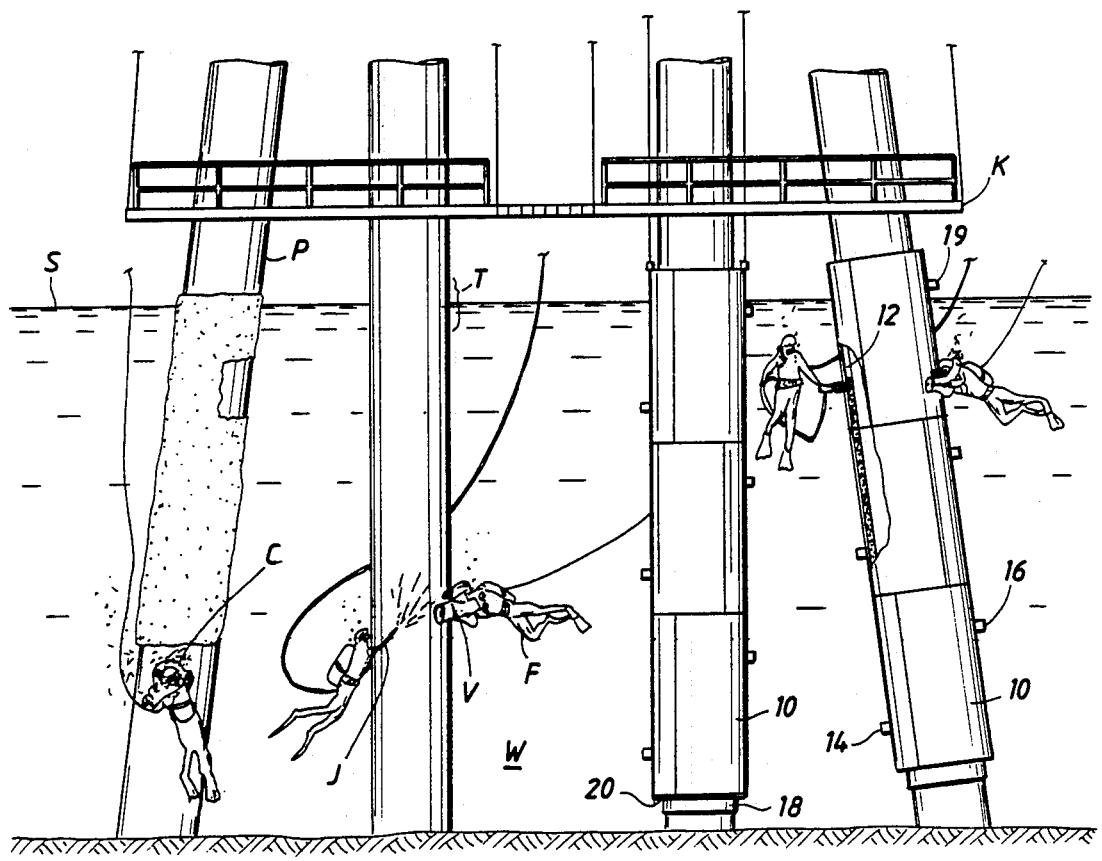
FIG. 3 is an elevation view illustrating certain steps performed during the encapsulation of the piles.

After desired placement of the jacket 10, suitable external support and reinforcing bands (not illustrated) may be installed about the jacket to provide additional reinforcing strength to the jacket 10 during filling with and curing of the epoxy. As best illustrated in FIG. 3, each of the jackets 10 is provided with one or more longitudinally spaced and angularly offset inlet ports 14 and 16. The ports 14 and 16 are preferably internally threaded to receive threaded closure plugs (not illustrated) after the epoxy grout has been injected, or for releasable connection with the epoxy mixing nozzle for filling, as will be described in greater detail hereinafter.

Preferably, the jackets 10 are made translucent in order that the divers F and video camera V may visually monitor the movement or flow of the epoxy grout to determine its level as it rises within the annular void V of the jacket 10 as well as being able to check for holidays and incomplete and uneven distribution of the flowable epoxy mix in the annular void 12. Transparent or translucent windows may be provided for visual and video monitoring if the jacket is not made translucent.

Jacket Installation

While the jacket 10 may be installed in a number of suitable ways, it is preferable for the jacket section to be assembled around the piles P above water line. Prior to or substantially simultaneously with positioning the jacket 10 about the pile a diver F can install a friction clamp 18 to the lower end of the pile P. The jacket 10 is then lowered until it is supported on the friction clamp 18 (FIG. 3) which also carries the lower grout seal 20. In the illustrated embodiment three jacket sections are assembled in an end-to-end sealed relationship above the friction clamp 10 which defines the portion of the pile P which is to be encapsulated by the epoxy grout. In this instance the encapsulation will extend above the tidal zone T.

Figure 4:
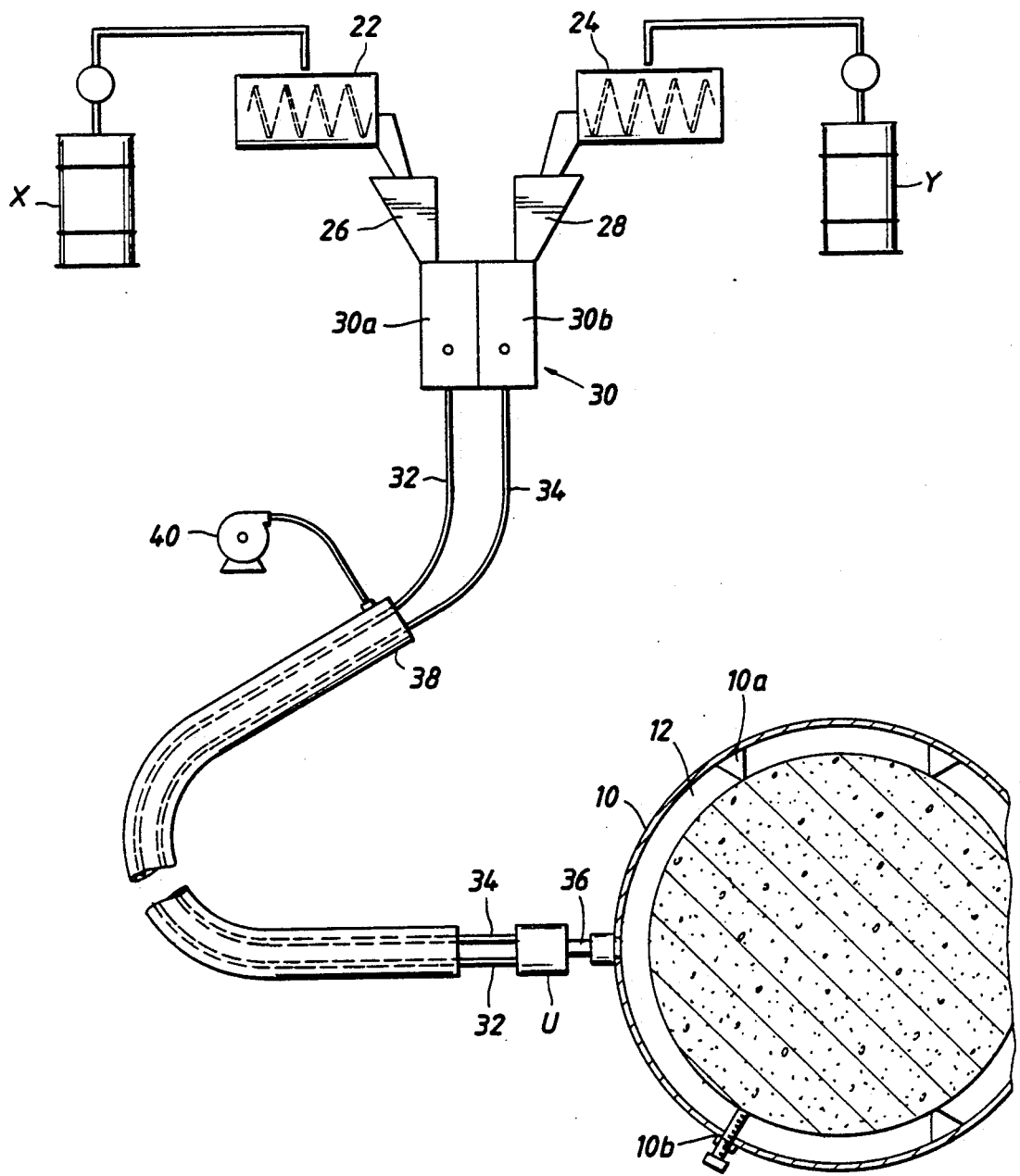
FIG. 4 is a schematic view of an epoxy grout supply system operably connected with a portion of a jacketed structural member in accordance with the present invention.

To allow assembly of the jacket above the water surface and subsequent lowering of the jacket 10 into place under the water surface, a plurality of threaded adjustable stand-off or centering lugs 10b may be installed through the jacket wall in addition to the fixed stand-offs 10a (FIG. 4). When the jacket 10 is placed around the pile P, the adjustable lugs 10b are positioned at their outermost limit, farthest from the center of the pile P. After the jacket is lowered to its final position, the adjustable lugs 10b (FIG. 4) are rotatably manipulated by the divers F outside the jacket 10 to properly create and maintain the desired annular void V.

In a method variation illustrated in FIG. 5, the lowermost end of the jacket 10 is placed slightly below the mudline M into cavity K, said cavity having been formed by high pressure water or sand blasting during the final cleaning phase described herein. The cavity K may be filled with epoxy grout to form a support pad or base Q for the jacket 10, if desired. In applications where it is not desired to extend the encapsulation to or below the mudline M, the jacket 10 may be terminated with a bottom seal mechanism 20 (FIG. 3) which is temporarily supported or mounted by the affixable clamp 18.

The Encapsulating Material

The preferred grouting or encapsulating material G is a
multiple component proprietary epoxy resin system sold under the "BRUTEM" 14 brand or trade name by I. W. Industries, P.0. Box 19452, Houston, Tex., 77224, although any multiple component polymer system which will properly cure under water may be used. The preferred grouting material G is formulated to provide low viscosity for pumpability and ease of injection and flow within the jacket 10 while providing high strength and bond to the pile P when curing under water. The encapsulating material or grout G is preferably field mixed of three components designated X component, Y component and Z component. The X component contains a polyamine curing agent as well as a curing accelerator and is provided with black pigments to obtain a uniform black coloring. The Y component contains the epoxy resin and is provided with a white pigmentation for providing a uniform white color. The Z component is an inert aggregate or filler of specially graded or sized inert silicate material (sand) that is separately blended into both the X and Y components. The premixing ratio is normally three to four parts by weight of component Z to one part of component X or to one part of component Y. The premixed components X and Y (hereinafter designated XZ or YZ) are kept separate after premixing with component Z until immediately prior to use.

After final mixing of the active components XZ and YZ, the resulting epoxy resin or grout has a workable or pot life of approximately one (1) hour at 77° Fahrenheit. When components XZ and YZ are finally mixed, at the injection nozzle, to be described hereinafter, a one to one ratio of components XZ and YZ is preferred.

The nominal engineering properties of the hardened or cured epoxy grout G include a minimum compressive strength of 4,500 psi at twenty-four (24) hours and 7,000 psi at seven (7) days. The seven (7) day tensile strength minimum is 1,000 psi while the flexural strength minimum at seven days is 3,000 psi. The bond strength to concrete using the disclosed test procedure is a minimum of 150 psi.

Mixing and Supply System Apparatus

The encapsulating material supply system is schematically illustrated in FIG. 4 operably connected to the form 10. The system includes two identical auger or paddle mixers 22 and 24 such as the series S60–S80 of Essex Manufacturing Co. These mixers have a capacity of eight (8) cubic feet and the mixing blades are powered by one and a half (1½) horse power pneumatic motors. The black X component is premixed with the sand or Z component in one paddle mixer 22 while the contrasting white Y component is premixed with the sand or component Z in the other mixer 24. As mentioned previously, the ratio of the X or Y component is preferably kept on a one to one basis and therefore equal amounts of Z component, normally four (4) parts aggregate to one (1) part by weight of wetted material or component X or Y, are mixed in each of the two mixers 22 and 24. When suitably premixed to a homogeneous uniform different coloring, the contents of the paddle mixer 22 and 24 are dumped into separate stainless steel supply hoppers 26 and 28 attached to the metering pump 30. The dual pumping chambered 30a an 30b metering pump 30 used is preferably a positive displacement pump and is preferably the model 206–445 manufactured by Graco having an input output pressure ratio of one to eleven. However, any suitable pump arrangement having separate output pumping chambers 30a and 30b for providing substantially equal volumes of the premixed XZ and YZ components is suitable. If desired, two separate pumps may be employed, but the two chambered Graco pump is preferred.

The dual positive displacement pump 30 provides a one to one ratio of the premixed components XZ and YZ to the separate and parallel conduits or hoses 32 and 34 which are connected to an operating manifold U having a static outlet mixer 36. To control the temperature of the premixed components XZ and YZ, the hoses 32 and 34 may be enclosed in an outer flexible sleeve 38 through which heated or cooling water may be circulated by pump 40. By controlling the temperature, the final properties of the encapsulating material G can be closely controlled and enhanced.

Mixing

To prevent or minimize premature set up, the final mixing of the premixed active components XZ and YZ to commence the polymerization process is done at the output mixer 36 of the discharge manifold U. The specific construction or arrangement of the manifold U is not critical. The manifold U will have at least two inlets connected to hoses 32 and 34 leading to a common or single outlet 36. Suitable quick acting valves may be provided as desired for controlling or directing the flow in the manifold U. The static mixer 36 is located at the output of manifold U for combining the premixed components XZ and YZ in a homogenous mixture. Preferably, a series connected pair of model 100 series static mixers manufactured by T H Industries and which is preferably teflon coated on the wetted mixing baffles or elements, is used. To insure complete and proper final mixing of the two grout components XZ and YZ and to commence or trigger the polymer or epoxy reaction, two or more of the static mixers 36 should be connected in series to the outlet of manifold 36. A uniform grey color effluent from the mixer 36 will indicate that proper mixing of the contrasting colored components XZ and YZ has occurred. For convenience, a solvent flush line (not illustrated) may be connected to the divers manifold U for flushing the mixer 36 of mixed epoxy. The diver or other manifold operator will also have suitable remote controls at the manifold to start and stop the supply pump 30.

Injection

When it is desired to inject the epoxy grout into the jackets, the mixed outlet 36 of the mixing manifold U is attached to the lower threaded inlet 14 of the lowest jacket section 10 by a diver F. Prior to connection, the diver F may have the pump 30 commence pumping to visually verify the proper mixing of the epoxy grout is occurring in the static mixer 36. When so assured by a uniform grey color of combined epoxy effluent of the premixed white component YZ and black component XZ, the diver F or operator may then threadedly connect the mixing manifold 36 with the lower port 14 of the bottom jacket 10. Filling of the annular void 12 between the jacket 10 and the pile P is then accomplished with the pump 30 by filling the jacket 10 from the bottom and displacing the water upwardly from the jackets 10 and out the upper port 16. The epoxy encapsulating material B being more dense or heavier than the water quickly displaces the water W upwardly from the void 12. As the grout G reaches the level at or immediately above upper nozzle 16 and begins to escape through the port 16 the pump 30 is stopped. After visually checking to insure the absence of voids in the grey colored epoxy through the translucent walls of the jacket 10, the mixer 36 is disconnected from the lower inlet port 14. The port 14 is then plugged and the mixing nozzle 36 is moved to the location of the port 16 which is preferably 180° offset from lower port 14. The process of filling the void 12 continues in sequence from lower nozzle to next adjacent upper nozzle until the entire column length of void 12 within the jackets 10 is filled with the pumpable encapsulating material G. By pumping the flowable encapsulating material or grout G upwardly in the annular void 12, a more dense and uniform structure is obtained and which prevents the formations of voids or holidays in the encapsulation that frequently results from simply pouring the epoxy into the top of the void.

In the event it is desired to encapsulate below the mudline M, the mud is jetted out to form a pocket K adjacent the pile P (FIG. 5) which is then cleaned in the usual manner. The pocket K is then filled with the encapsulating material G to encapsulate about the portion of the pile P below the mudline M and to form an enlarged landing base Q for the jacket 10. Before the epoxy has fully hardened, the jacket 10 is lowered down the pile P until it rests on the epoxy base Q in cavity K, which also serves as the lower seal.

As best illustrated in FIG. 7, when it is desired to inject the epoxy grout G into a jacket 110 around horizontal or near horizontal structural members A the outlet of the mixing nozzle 36 is connected to the threaded injection port 114 nearest to one end of the jacket 110 and the void 12 between the jacket 10 and the cap beam or girder A is filled with epoxy grout by activating the pump 30. The epoxy grout G flows or progresses horizontally and vertically to completely fill the void 12. As the grout G reaches the level immediately adjacent to injection port 116 and begins to escape through port 116, the pump 30 is stopped. After visually checking to insure the absence of voids in the grey colored epoxy grout through the translucent jacket 110, the mixer nozzle 36 is disconnected from injection port 114 and moved to port 116. The process of filling the void 12 continues in sequence from port to port in horizontally consecutive fashion until the entire length of void 12 within jacket 10 is filled with epoxy grout G to the desired height.

Flushing

When submerged or partially submerged members are to be encapsulated in bio-active marine environments, the annular void 12 within the jacket 10 may be flushed with a solution of biological inhibitor immediately following the final phase of cleaning. The solution is pumped through the lowermost injection port 14 (FIG. 3) while all other ports are temporarily closed with threaded plugs to a point immediately above the waterline W. The solution is pumped with sufficient velocity and volume to displace, or properly co-mingle with, the standing water W within the void 12. The displaced water is allowed to escape the jacket 10 by overflowing the jacket or passing through an injection port 19, situated above the waterline W. The solution containing the biological inhibitor is allowed to remain in the annular void 12 until the injection process described hereinabove is initiated.

Testing

At various predetermined or randomly selected intervals within the course of a specific encapsulation project, the in-situ bond strength between the encapsulation material or grout G and the pile P, may be determined or verified by the test apparatus method illustrated in FIG. 7. Circular test dollies or attachment devices 42 for the test instrument are affixed or bonded at chosen locations on the outside surface of jacket 10. Preferably, the dollies 42 are attached to the jacket 10 at random locations. After the epoxy grout G has been injected in place and has reached a predetermined test maturity or curing time, preferably seven days from time of injection, a portion of the completed encapsulation is isolated into a test section by cutting or coring a circular groove 43 around a known bonding surface area 44 of the grout G to the pile P adjacent the test dolly 42. The circular groove 43 is cored or cut through the jacket 10 and the epoxy grout E until the surface of the encapsulated member P is reached. The resulting test section 46 has a known bonding surface area 44 at its point of contact with the encapsulated member P and that known area 44 is usually identical to that of the circular base 42 of the test dolly 42.

To determine the bond strength between the test section 46 and surface of the encapsulated member P, a test instrument or apparatus 50 is positioned by the diver F over the test dolly 42 to attach the securing jaw 52 of the test apparatus 50 with the test dolly 42. The test instrument 50 is essentially disclosed in U.S. Pat. No. 3,527,093 to Sellers and which disclosure is, totally incorporated herein for all purposes by this specific reference. The present test instrument 50 has a central body 54 and is modified from the Sellers instrument by a plurality of outward extending stabilizing and loading legs 56 of more suitable design for pushing against the jacket 10 during operation. The securing jaw 52 is attached to a rotatable threaded power screw 58 operable mounted with the body 54 and having an operating lever or knob 60. For further details of the construction and operation instrument apparatus 50, see U.S. Pat. No. 3,527,093. The diver or other operator then applies a tensile loading to the test dolly 42 by rotating lever or knob 60 on the test apparatus 50 while visually monitoring the tensile load on calibrated scale 62. In a change from the patented Sellers instrument, the scale 62 is calibrated to directly read the separation bonding stress as determined by the total tensile load, divided by the known bonded surface area 42a of the test section, and is directly expressed in stress units of pounds per square inch (psi). This enables rapid field determination with no need for calculation or error that may be made in doing so.

To verify that the bonding strength has reached a certain minimum level, a slightly different technique is used. A movement limit stop is placed on the helically threaded force applying screw 58 to limit its movement to apply no greater than the minimum acceptable bonding strength a tensile force stress. If the epoxy grout G and test dolly 42 does not separate from the structural member P, the strength of the bond is verified as greater than the specified minimum acceptable. This technique has an additional preferred advantage in that it is non-destructive.

Various modifications and alterations in the described structures and methods will be apparent to those skilled in the art of the foregoing description and which do not depart from the spirit of the invention. For this reason, such changes are desired to be included in the appended claims. The appended claims recite the only limitation to the present invention and the descriptive manner which is employed for setting forth the embodiments and is to be interpreted as illustrative and not limitative.

What is claimed is:

1. A method of forming a protective encasement about at least a portion of a load supporting structural member which is at least partially submerged in water, comprising the steps of:

provided a jacket of reinforced resin material which is essentially chemically inert and corrosion resistant;

positioning the jacket about the portion of the structural member desired to be encapsulated while separating the jacket from the structural member a desired predetermined distance to form a continuous annular void;

preparing a first component of a epoxy grout at a location remote from the structural member;

preparing a second component of an epoxy grout at a location remote from the structural member;

pumping the first epoxy grout component through a first conduit to a location adjacent said jacket;

pumping the second epoxy grout component through a second conduit to a location adjacent said jacket;

combining the first epoxy grout component with the second epoxy grout component to initiate the epoxy polymerization reaction immediately prior to injecting the combined epoxy grout into the jacket at a submerged location in the water to fill the continuous annular void.

2. The method set forth in claim 1 wherein, the combined epoxy grout flows upwardly in the annular void to displace water from the annular void.

3. The method as set forth in claim 1 wherein, the combined epoxy grout bonds to the jacket to form a unitary structure.

4. The method as set forth in claim 1 wherein, the combined epoxy grout bonds to the structural member to form a unitary encapsulation.

5. The method as set forth in claim 1 wherein, the combining of the first epoxy grout component with the second epoxy grout component produces a uniform visible coloring indicating the proper mixing of the components.

6. The method as set forth in claim 5, wherein the uniform visible coloring of the components after combining is visible through the translucent jacket to visually indicate the presence of the mixed epoxy encapsulation.

7. The method as set forth in claim 1, wherein the step of providing includes the providing of a jacket at least partially formed of translucent material to enable visual monitoring of the presence of the properly mixed combined grout injected into the jacket.

8. The method as set forth in claim 1, including: coloring the first component of the epoxy grout with a first color.

9. The method as set forth in claim 1, including: coloring the second component of the epoxy grout with a color.

10. The method as set forth in claim 8, including the step of:
coloring the second component of the epoxy grout with a second color to produce a combined grout of a third color.

11. The method as set forth in claim 10, including the step of:
producing a uniform third color of epoxy grout when the first epoxy grout component and the second epoxy grout component are properly mixed.

12. A method of forming a protective encasement about a portion of a structural member, comprising the steps of:
providing a jacket to contain the encasement material;
positioning the jacket about the portion of the structural member desired to be encased while separating the jacket from the structural member a desired predetermined distance to form a continuous annular void for receiving the encasement material;
preparing a first component of an encasement material at a location remote from the structural member;
preparing a second component of an encasement material at a location remote from the structural member;
pumping the first encasement material component through a conduit to a location adjacent said jacket;
pumping the second encasement material component through a second conduit to a location adjacent said jacket; and
combining the first encasement material component with the second casement material component to initiate the solidification reaction immediately prior to injecting the combined encasement material into the jacket to fill the continuous annular void while preventing undesired solidification of the encasement material exteriorly of the jacket.

13. The method as set forth in claim 12, including the step of:
flowing the combined encasement material upwardly in the void to enhance the engineering properties of the combined encasement material in the jacket.

14. The method as set forth in claim 12, wherein the step of preparing the first component includes the step of:
coloring the first component with a first color.

15. The method as set forth in claim 14, wherein the step of preparing the second component includes the step of:
coloring the second component with a second color that produces a third color when the second component is combined with the first component.

16. The method as set forth in claim 15, wherein:
monitoring the uniformity of the third coloring to insure proper mixing when combining the first component with the second component.

17. A method of forming a protective encasement about a portion of a structural member, comprising the steps of:
providing a jacket to contain the encasement material;
positioning the jacket about the portion of the structural member desired to be encapsulated while separating the jacket from the structural member a desired predetermined distance to form a continuous void for receiving the encasement material;
preparing a first component of an encasement material with a first color at a location remote from the structural member;
preparing a second component of an encasement material at a location remote from the structural member;
pumping the first encasement material component through a conduit to a location adjacent said jacket;
pumping the second conduit to a location adjacent said jacket;
combining the first encasement material component with the second encasement material component to initiate the solidification reaction immediately prior to injecting the combined encasement material into the jacket to fill the continuous annular void; and visually monitoring the color of the combined encasement material in the jacket to verify proper mixing of the first component with the second component.

18. The method as set forth in claim 17, wherein the steps of preparing the second component includes the steps of:
coloring the second component with a second color to produce a third color for visual monitoring the combined encasement material.

19. The method as set forth in claim 18, wherein a uniform third color indicates proper mixing of the first component and second component to form the combined encasement material.

20. A method of forming a protective encasement about a portion of a structural member, comprising the steps of:
providing a substantially translucent jacket to contain the encasement material;
positioning the jacket about the portion of the structural member desired to be encapsulated while separating the jacket from the structural member a desired predetermined distance to form a continuous void for receiving the encasement material;
preparing a first component of an encasement material at a location remote from the structural member;
preparing a second component of an encasement material at a location remote from the structural member;
pumping the first encasement material component through a conduit to a location adjacent said jacket;
pumping the second encasement material component through a second conduit to a location adjacent said jacket;
combining the first encasement material component with the second encasement material component to initiate the solidification reaction immediately prior to injecting the combined encasement material into the jacket to fill the continuous annular void; and
visually monitoring the presence of the combined encasement material in the translucent jacket to verify proper mixing of first and second components and filling of the annular void for obtaining proper encapsulation.

21. The method as set forth in claim 20, including the step of:
coloring the combined encasement material to visually indicate presence in the translucent jacket.

22. A method of forming a protective encasement about a portion of a structural member, comprising the steps of:
providing a jacket to contain the encasement material;
positioning the jacket about the portion of the structural member desired to be encapsulated while separating the jacket from the structural member a desired predetermined distance to form a continuous void for receiving the encasement material;
preparing a first component of an encasement material at a location remote from the structural member;
preparing a second component of an encasement material at a location remote from the structural member;
pumping the first encasement material component through a conduit to a location adjacent said jacket;
pumping the second encasement material component through a second conduit to a location adjacent said jacket;
combining the first encasement material component with the second encasement material component to initiate the solidification reaction immediately prior to injecting the combined encasement material into the jacket to fill the continuous annular void while preventing undesired solidification of the encasement material exteriorly of the jacket; and
flowing the combined encasement material upwardly in the continuous void to effect filling prior to hardening of the encasement material.

23. The method as set forth in claim 22, further including:
injecting the combined encasement material initially into the jacket adjacent the lower most end of the jacket for filling the continuous void.

24. The method as set forth in claim 23, further including:
filling the continuous void with the combined encasement material to a level in the jacket above the location of the initial injection into the jacket.

25. The method as set forth in claim 24, including:
interrupting the steps of combining and injecting to move the location of injection of the combined encasement material to a location adjacent the level of encasement material in the jacket; and
resuming the steps of combining and injecting for continuing to flow upwardly the combined encasement material for filling the continuous void.
said jacket having a fill port formed thereon communicating with said continuous void for directing flow of the encasing grout into said continuous void for filling said continuous void with upwardly flow.

* * * * *